United States Patent
Duprat de Paule et al.

(10) Patent No.: US 6,878,665 B2
(45) Date of Patent: Apr. 12, 2005

(54) DIPHOSPHINES, THEIR COMPLEXES WITH TRANSISITION METALS AND THEIR USE IN ASYMMETRIC SYNTHESIS

(75) Inventors: Sébastien Duprat de Paule, Paris (FR); Nicolas Champion, Dijon (FR); Virginie Vidal, Paris (FR); Jean-Pierre Genet, Verrieres-le-Buisson (FR); Philippe Dellis, Dijon (FR)

(73) Assignee: Synkem, Chenove (FR)

( * ) Notice: Subject to any disclaimer, the term of this patent is extended or adjusted under 35 U.S.C. 154(b) by 0 days.

(21) Appl. No.: 10/490,409

(22) PCT Filed: Sep. 16, 2002

(86) PCT No.: PCT/FR02/03146
§ 371 (c)(1),
(2), (4) Date: Mar. 23, 2004

(87) PCT Pub. No.: WO03/029259
PCT Pub. Date: Apr. 10, 2003

(65) Prior Publication Data
US 2004/0260101 A1 Dec. 23, 2004

(30) Foreign Application Priority Data
Sep. 28, 2001 (FR) .............................. 01 12499

(51) Int. Cl.[7] .......................... B01J 31/00; C07F 15/00; C07F 9/02; C07C 29/14
(52) U.S. Cl. ....................... 502/165; 502/166; 549/212; 549/220; 549/221; 556/21; 556/23; 568/15; 568/17; 568/881; 568/885
(58) Field of Search ................. 502/165, 166; 549/212, 220, 221; 556/21, 23; 568/15, 17, 881, 885

(56) References Cited

U.S. PATENT DOCUMENTS 5,872,273 A * 2/1999 Saito et al. ................. 556/21
6,043,380 A * 3/2000 Okeda et al. ............... 549/206
6,333,291 B1 * 12/2001 Yokozawa et al. ......... 502/162

FOREIGN PATENT DOCUMENTS

EP   0 850 945 A1   7/1998

OTHER PUBLICATIONS

Pai, et al. Synthesis of new chiral diposphine ligand (Bis-benzodioxanPhos) and Its application In asymmetric catalytic hydrogenation. Tetrahedron Letters, Elsevier Science Publishers, Amsterdam, NL,vol. 43, No. 15 pp. 2789–2792 (2002).

Tsivunin, et al "Phosphorylation of 1, 4–benzodiozane" Journal of General Chemistry USSR., vol. 51, No. 7, pp. 1317–1319 (1981).

* cited by examiner

Primary Examiner—Porfirio Nazario-Gonzalez
(74) Attorney, Agent, or Firm—Antonelli, Terry, Stout & Kraus, LLP

(57) ABSTRACT

The invention relates to novel diphosphines, in optically pure or racemic form, of formula (I):

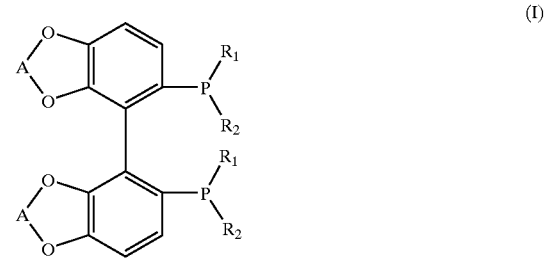

in which:
$R_1$ and $R_2$ are a ($C_5$–$C_7$)cycloalkyl group, an optionally substituted phenyl group or a 5-membered heteroaryl group; and
A is ($CH_2$—$CH_2$) or $CF_2$.

The invention further relates to the use of a compound of formula (I) as a ligand for the preparation of a metal complex useful as a chiral catalyst in asymmetric catalysis, and to the chiral metal catalysts comprising at least one ligand of formula (I).

23 Claims, No Drawings

DIPHOSPHINES, THEIR COMPLEXES WITH TRANSISITION METALS AND THEIR USE IN ASYMMETRIC SYNTHESIS

This application is a 371 of International Application No. PCT/FR02/03146 designating the United States.

The present invention relates to novel racemic or chiral diphosphines useful as bidentate ligands in the synthesis of metal complexes and, more particularly, catalysts intended especially for catalytic asymmetric hydrogenation.

Asymmetric catalysis has the advantage of affording the direct preparation of optically pure isomers by asymmetric induction without the need to resolve racemic mixtures. The prior art has already described certain diphosphorus ligands commonly used in the preparation of metal complexes for the asymmetric catalysis of hydrogenation reactions, carbonylation reactions, hydrosilylation reactions, reactions for the formation of C—C bonds or even reactions for the asymmetric isomerization of allylamines. 2,2'-Bis(diphenylphosphino)-1,1'-binaphthyl (BINAP) or [(5,6),(5',6')-bis(methylenedioxy)biphenyl-2,2'-diyl]bis-(diphenylphosphine) (SEGPHOS), described in the patent application published under the number EP 850 945, may be mentioned in particular.

It is desirable to develop novel chiral ligands in order to improve the selectivity of reactions (diastereoselectivity and enantioselectivity).

The present invention therefore relates to novel diphosphine derivatives, in racemic or optically pure form, of formula (I):

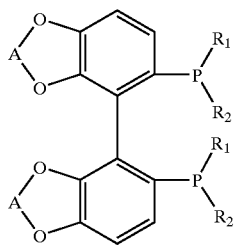

(I)

in which:

$R_1$ and $R_2$ each independently are:

a ($C_5$–$C_7$)cycloalkyl group, a phenyl group optionally substituted by one or more ($C_1$–$C_4$)alkyl, ($C_1$–$C_4$)alkoxy or di($C_1$–$C_4$)alkylamino groups or by a halogen atom, or a 5-membered heteroaryl group; and A is an ethylene group ($CH_2$—$CH_2$) or a $CF_2$ group.

5-Membered heteroaryl group is understood as meaning e.g. a 2-furanyl, 3-furanyl, 2-benzofuranyl or 3-benzofuranyl group.

Alkyl is understood as meaning a linear or branched, saturated hydrocarbon group.

($C_1$–$C_4$)alkyl is understood as meaning an alkyl group containing from 1 to 4 carbon atoms.

The term 'alkoxy' denotes an O-alkyl radical in which alkyl is as defined above.

Halogen atom is understood as meaning a chlorine, bromine, fluorine or iodine atom.

According to one particular feature, the present invention relates to the compounds of formula (I) in which $R_1$ and $R_2$ are identical and, more particularly, in which $R_1$ and $R_2$ are identical and are a phenyl group.

The compounds of formula (I) according to the present invention can be prepared by the process shown in SCHEME 1 below, in which $R_1$, $R_2$ and A are as defined for (I) and R is a ($C_1$–$C_4$)alkyl group or an optionally substituted phenyl group.

SCHEME 1

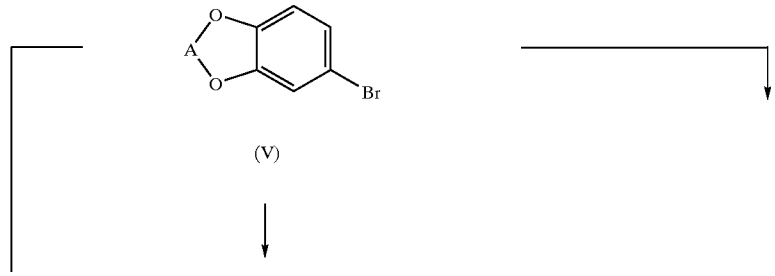

(V)

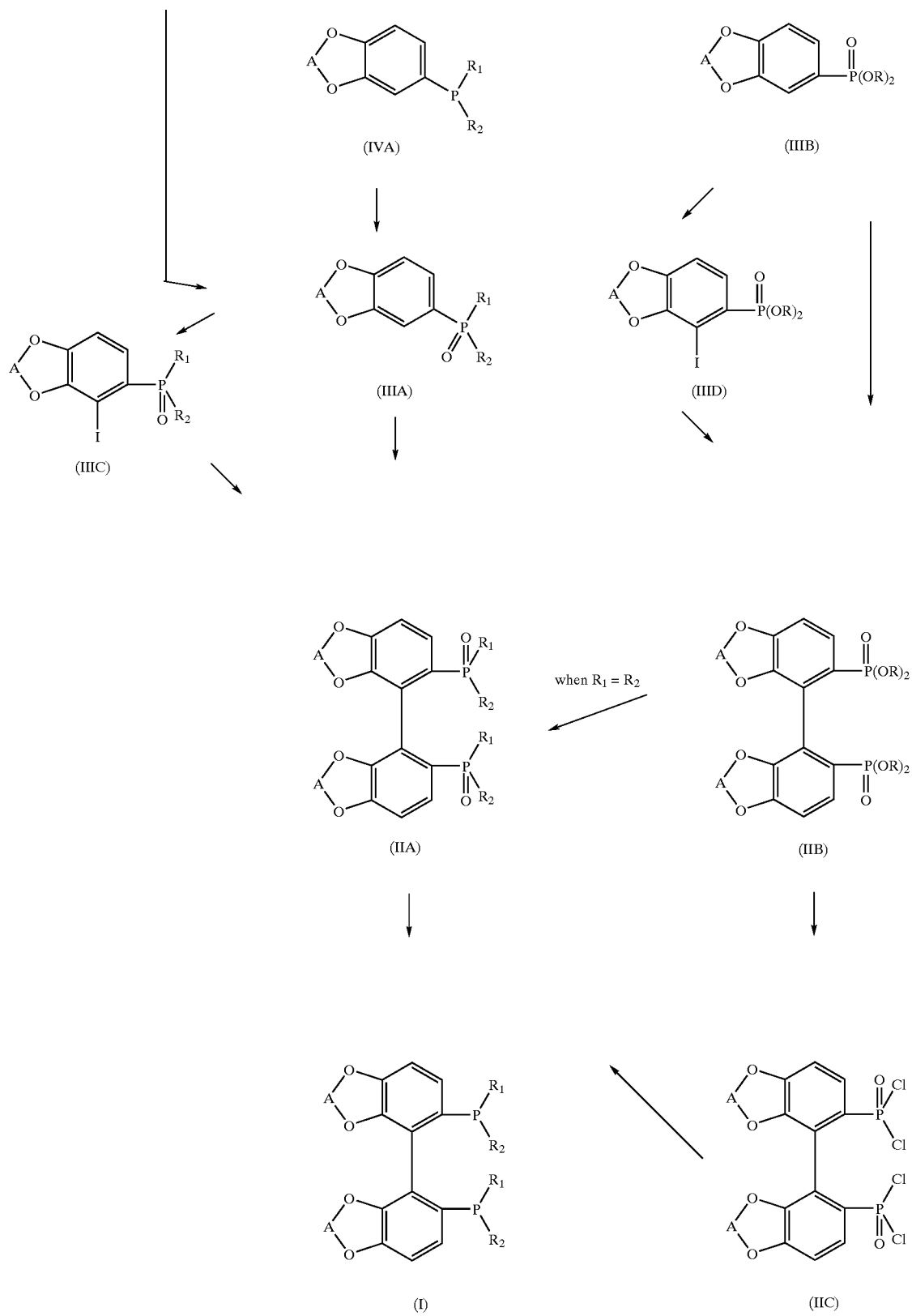

The compound of formula (I), in optically pure form, (R) or (S), or in racemic form, can be prepared by reducing the compound of formula (IIA):

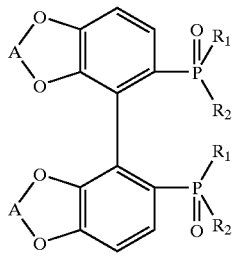

(IIA)

in which $R_1$, $R_2$ and A are as defined for (I), respectively in the corresponding optically pure form, (R) or (S), or in the racemic form, for example by reaction with a reducing agent, such as trichlorosilane, in the presence of an amine, such as tributylamine.

The compound (IIA) in optically pure form is obtained e.g. by resolving the compound (IIA) in racemic form via the formation of a complex with (−)-L-dibenzoyltartaric acid or (+)-D-dibenzoyltartaric acid or with other chiral acids, as described in the prior art for this type of resolution.

The enantiomers can also be prepared by separation via chiral phase chromatography.

The compounds of formula (IIA), in racemic or optically pure form, which are intermediates in the synthesis of the compounds of formula (I), are novel compounds and form an integral part of the invention.

The compounds of formula (IIA) can be prepared from the compounds (IIIA):

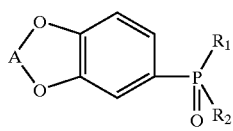

(IIIA)

in which $R_1$, $R_2$ and A are as defined for (I), by reaction with an organolithium compound, such as tert-butyllithium, in the presence of iron trichloride or another appropriate oxidizing agent.

The compounds (IIA) can also be prepared from the derivative (IIIA) in two steps: iodination of the compound (IIIA) to give an iodine derivative of formula (IIIC), followed by an Ullman-type coupling reaction with the aid of copper.

The compounds (IIA) in which $R_1$ and $R_2$ are identical can be prepared in a third way from the compounds of formula (IIB) in which R is a $(C_1-C_4)$alkyl group or a substituted or unsubstituted phenyl group. In this third process the compounds (IIB) are brought into contact with an organometallic compound of the formula $R_1Li$ or $R_1MgX$, in which $R_1$ is as defined for (I) and X is a halogen atom.

The compounds (IIB) can exist in racemic or chiral form and can be resolved, like the compounds of formula (IIA), via chiral acids or chiral phase chromatography.

The compounds of formula (IIB) are novel and form an integral part of the invention.

The compounds (IIA) in which $R_1$ and $R_2$ are identical can also be prepared from the compounds of formula IIB by a 2-step process of which the first step consists in reacting said compound IIB with thionyl chloride, in the presence of a solvent, to give the halogen derivative (IIC):

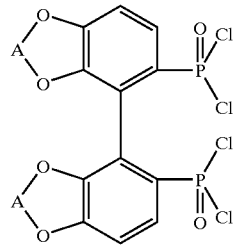

(IIC)

and the second step consists in reacting said compound IIC with an organometallic compound, especially an organolithium compound of the formula $R_1Li$ or an organomagnesium compound of the formula $R_1MgX$, in which $R_1$ is as defined for (I) and X is a halogen atom, to give the expected compound of formula IIA.

The compound of formula (IIIA) can be prepared by oxidizing the phosphine of formula (IVA):

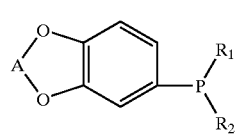

(IVA)

in which $R_1$, $R_2$ and A are as defined for (I), by reaction with a solution of hydrogen peroxide in methanol or with the aid of other phosphine-oxidizing reagents well known to those skilled in the art.

The phosphine (IVA) itself can be prepared from the corresponding bromine compound (V) by reaction with an organolithium compound, such as n-butyllithium, and then with the phosphine $R_1R_2PCl$, where $R_1$ and $R_2$ are as defined for (I), at a temperature close to −70° C.

The compound (IIIA) can also be prepared directly from the compound (V) by reaction with magnesium in tetrahydrofuran to form a Grignard reagent, followed by reaction with the phosphinyl chloride $R_1R_2P(O)Cl$, where $R_1$ and $R_2$ are as defined for (I).

The compound (IIIA) can also be prepared from the compound (V) via the compound (IVA) by reaction with magnesium in tetrahydrofuran to form a Grignard reagent, followed by reaction with the phosphine $R_1R_2PCl$, where $R_1$ and $R_2$ are as defined for (I), and then by an oxidation reaction with a solution of hydrogen peroxide in methanol or with the aid of other phosphine-oxidizing reagents well known to those skilled in the art.

The compounds of formulae (IIIA), (IIIC) and (IVA) are novel and form an integral part of the invention.

The derivatives of formula (IIB) can be obtained in one step from the derivative (IIIB), in which R is as defined for the derivative (IIB), by reaction with an organolithium compound, such as sec-butyllithium, in the presence of iron trichloride or another appropriate oxidizing agent.

The derivatives of formula (IIB) can also be obtained in two steps from the derivatives of formula (IIIB) by iodination to give the iodine derivatives (IIID), followed by an Ullman-type reaction with copper to give the derivatives (IIB).

The compounds of formula (IIIB) can be obtained from the compounds of formula (V) by reaction with magnesium in an ether to form an organomagnesium compound, and reaction of the latter with a derivative Cl—P(O)(OR)$_2$, in which R is as defined in (IIB).

The compounds of formula (IIIB) can also be obtained from the compounds of formula (V) by reaction with nickel chloride at a temperature in the order of 100 to 160° C., in the presence of a derivative P(OR)$_3$, in which R is as defined for (IIB).

The compounds (IIIB) in which A is CF$_2$ are novel and form an integral part of the invention. The compounds (IIIB) in which A is ethylene and R is a phenyl, methyl or (C$_3$–C$_4$)alkyl group are novel and form an integral part of the invention.

A further feature of the invention relates to the use of a compound of formula (I) as a ligand for the preparation of a metal complex useful as a chiral catalyst in asymmetric catalysis.

The present invention further relates to the chiral metal catalysts comprising at least one ligand of formula (I) in racemic or, preferably, optically pure form. In the case where the ligand of formula (I) is in racemic form, the chirality of the metal complex is obtained via another chiral ligand, for example of the chiral diamine type.

The metal catalysts according to the present invention may be used for the asymmetric catalysis of hydrogenation reactions, hydroboronation reactions of unsaturated compounds, olefin isomerization reactions, allylic alkylation reactions and, in general, reactions for the formation of C—C bonds (such as 1,4-additions of boronic acids), reactions for the asymmetric cyclization of 4-pentenals (J. Org. Chem. 2000, 65, 5806–16), ene-yne cyclization reactions (Angew. Chem., Int. Ed. 2001, 40(1), 249–53), allylic substitution reactions of enolates (Angew. Chem., Int. Ed. 2000, 39(19), 3494–7) and reactions for the formation of aromatic α-amino acids (Angew. Chem., Int. Ed. 2000, 39(22), 4114–6).

In one preferred embodiment of the invention, the metal catalysts are used for the hydrogenation of C=O, C=C and C=N bonds. The catalysts which can be used in this type of reaction are preferably rhodium, ruthenium, palladium, iridium, nickel or copper catalysts.

In one particular embodiment, the invention relates to the chiral metal catalysts of formula (VI):

$$M_m L_n X_p S_q \qquad (VI)$$

in which:
M is a metal selected from rhodium, ruthenium, iridium, palladium, nickel and copper;
L is a chiral compound (I); and
X, S, m, n, p and q are defined as follows:
  if M=Rh, then X=Cl, Br or I; m=n=p=2; q=0;
  if M=Ru, then: X=—OC(O)CH$_3$; m=n=1; p=2; q=0;
    or X=Br; m=n=1; p=2; q=0;
    or X=Cl; S=N(CH$_2$CH$_3$)$_3$; m=n=2; p=4; q=1;
    or X=methylallyl; m=n=1; p=2; q=0;
    or X=Cl; S=pyridine; m=n=1; p=q=2;
    or X=Cl; S=chiral 1,2-diamine; m=n=1; p=q=2 or p=2, q=1;
  if M=Ir, then X=Cl, Br or I; m=n=p=2; q=0;
  if M=Pd, then: X=Cl; m=n=1; p=2; q=0;
    or X=π-allyl; m=n=p=2; q=0;
  if M=Ni, then X=Cl, Br or I; m=n=1; p=2; q=0.

Examples of chiral diamines which may be mentioned are (R,R)- and (S,S)-1,2-diphenylethylenediamine.

One particular feature of the invention relates to the metal catalysts of formula (VII):

$$[M_r L_s Z_t W_u] Y_v \qquad (VII)$$

in which:
M is a metal selected from rhodium, ruthenium, iridium, palladium and copper;
L is a chiral compound (I); and
Z, W, r, s, t, u and v are defined as follows:
  if M=Rh, then Z=1,5-cyclooctadiene or norbornadiene; Y=BF$_4$, ClO$_4$, PF$_6$, OTf or BPh$_4$; r=s=t=v=1; u=0;
  if M=Ru, then: Z=Cl, Br or I; W=benzene or p-cymene; Y=Cl, Br or I; r=s=t=u=v=1;
    or Y=BF$_4$, ClO$_4$, PF$_6$ or BPh$_4$; r=s=1; t=u=0; v=2;
    or Z=Cl; Y=NH$_2$(C$_2$H$_5$)$_2$; r=s=2; t=5; u=0; v=1;
  if M=Ir, then Z=1,5-cyclooctadiene or norbornadiene; Y=BF$_4$, ClO$_4$, PF$_6$ or BPh$_4$; r=s=v=1; t=1; u=0;
  if M=Pd, then Y=BF$_4$, ClO$_4$, PF$_6$ or BPh$_4$; r=s=v=1; t=u=0;
  if M=Cu, then Y=PF$_6$ or ClO$_4$; r=s=v=1; t=u=0.

The rhodium or ruthenium catalysts are currently preferred, particularly if selected from those given below:
the compounds of form (VI):
  in which M=Ru and X=Br; m=n=1; p=2; q=0;
  or X=Cl; S=N(CH$_2$CH$_3$)$_3$; m=n=1; p=4; q=1;
  or X=Cl; S=pyridine; m=n=1; p=q=2; and
the compounds of formula (VII):
  in which M=Rh and Z=1,5-cyclooctadiene or norbornadiene; Y=BF$_4$, ClO$_4$, PF$_6$, OTf or BPh$_4$; r=s=t=v=1; u=0.

The catalysts comprising a ligand of formula (I) according to the invention and a metal selected from rhodium, ruthenium, palladium, iridium, nickel and copper can be prepared by processes described in the literature that are well known to those skilled in the art. Reference may be made in particular to the patent application published under the number EP 850 945.

The catalysts according to the invention are generally prepared from a starting metal complex whose nature varies according to the metal selected.

In the case of the rhodium catalysts, the starting complex is e.g. one of the following compounds: Rh(cod)$_2$OTf; [Rh(cod)Cl]$_2$, where cod denotes 1,5-cyclooctadiene; Rh(acac)(CO)$_2$, where acac denotes acetylacetonate; or Rh(acac)(C$_2$H$_4$)$_2$.

Complexes such as RuCl$_3$, Ru(cod)(methylallyl)$_2$, [RuCl$_2$(benzene)]$_2$ and [RuCl$_2$(nbd)]$_x$, where nbd represents norbornadiene and x is an integer, may be used to prepare the ruthenium catalysts. Ru(acac)$_3$ and [RuCl$_2$(cod)]$_x$, where x is an integer, may also be mentioned.

In general terms, the metal catalysts according to the invention are prepared by mixing the starting metal complex, a ligand of formula (I) and a degassed, anhydrous organic solvent and optionally maintaining the reaction mixture at a temperature of between 15 and 150° C., preferably of between 30 and 120° C., for e.g. 10 minutes to 5 hours.

Solvents which may be used are aromatic hydrocarbons (such as benzene, toluene or xylene), amides (such as formamide, dimethylformamide, dimethylacetamide, N-methyl-2-pyrrolidinone or hexamethylphosphorylamide), alcohols (such as ethanol, methanol, n-propanol or isopropanol) and mixtures thereof, ketones (such as acetone, methyl ethyl ketone, methyl isobutyl ketone or cyclohexanone), ethers (such as e.g. tetrahydrofuran) and linear, branched or cyclic alkanes (such as pentane, hexane or methylcyclohexane).

The catalyst is then isolated by conventional techniques (filtration or crystallization) and used in asymmetric reactions. Nevertheless, the catalyst can also be prepared in situ.

In this case the reaction which is to be catalyzed by the catalyst prepared in this way can be carried out without intermediate isolation of the catalyst.

The present invention further relates to the use of the metal catalysts according to the present invention for the catalysis of asymmetric reactions, especially hydrogenation reactions and reactions for the formation of C—C bonds. The asymmetric hydrogenation processes or processes for the asymmetric formation of C—C bonds which use such catalysts form an integral part of the invention. These processes are carried out under conditions well known to those skilled in the art.

For example, in the case of an asymmetric hydrogenation reaction, the unsaturated substrate, dissolved in a solvent containing the catalyst, is placed under hydrogen pressure. The operating conditions are analogous to those commonly used with the metal catalysts of the prior art. For example, a hydrogen pressure of between 1 and 150 bar and a temperature of 0° C. to 150° C. will be used. The molar ratio of substrate to catalyst generally varies from 1/100 to 1/100,000 and preferably from 1/100 to 1/5000.

The rhodium complexes prepared from the ligands of the invention are more particularly suitable for the asymmetric catalysis of olefin isomerization reactions, reactions for the hydrogenation of C=C bonds and 1,4-addition reactions of boronic acids.

The ruthenium complexes prepared from the ligands of the invention are more particularly suitable for the asymmetric catalysis of reactions for the hydrogenation of carbonyl bonds, C=C bonds and C=N bonds.

In the Examples which follow, 'Preparation' denotes the Examples describing the synthesis of intermediates and 'Example' denotes those describing the synthesis of compounds of formula (I), (VI) or (VII) according to the invention. These Examples serve to illustrate the invention and cannot under any circumstances limit its scope. The melting points are measured on a Koffler bench and the nuclear magnetic resonance spectral values are characterized by the chemical shift $\delta$ calculated relative to TMS, by the number of protons associated with the signal and by the shape of the signal (s for singlet, d for doublet, t for triplet, m for multiplet, dd for doublet of doublets, ddd for doublet of doublet of doublets, q for quadruplet, qd for doublet of quadruplets, J for coupling constant). The operating frequency and the solvent used are indicated for each compound. The mass spectrometry results are obtained with a Hewlett Packard 7989 A instrument.

The following abbreviations are used: RT=room temperature, DMSO=dimethyl sulfoxide, Ph=phenyl, THF=tetrahydrofuran, Me=methyl, Et=ethyl, acac=acetylacetonate, Tf=triflate; S-DPED=(S,S)-diphenylethylenediamine.

The nomenclature used to identify the compounds is that recommended by Chemical Abstracts.

Preparation 1

6-Bromo-2,3-dihydro-1,4-benzodioxin, Compound V 35 g of 1,4-benzodioxane and 200 ml of anhydrous dimethylformamide are placed under argon at 0° C. 54.9 g of N-bromosuccinimide are then added in portions. After it has returned gradually to room temperature, the reaction mixture is stirred for 24 hours. The solvents are evaporated off under reduced pressure and the white solid obtained is washed with dichloromethane. The filtrate is treated with 50 ml of saturated aqueous sodium sulfate solution, washed with 50 ml of saturated aqueous sodium chloride solution and dried over magnesium sulfate. After evaporation of the solvents under reduced pressure, a yellow oil is obtained (quantitative yield).

EI mass spectrum: $M^+=214$ $^1H$ NMR (200 MHz) $CDCl_3$: 4.25 (4H, s); 6.74 (1H, d); 6.93 (1H, dd); 7.02 (1H, d)

Preparation 2

6-Bromo-2,3-dihydro-1,4-benzodioxin, Compound V

Compound V can also be prepared by the following procedure:

5 g of 1,4-benzodioxane and 100 ml of anhydrous tetrahydrofuran are placed under argon in the dark. 5.12 g of 1,3-dibromo-5,5-dimethylhydantoin are then added. The reaction mixture is stirred at room temperature in the dark for 18 hours. After half of the tetrahydrofuran has been evaporated off, 50 ml of pentane are added. After filtration, the operation is repeated three times and the solvents are then evaporated off under reduced pressure. The oily residue obtained is purified by chromatography on a silica gel column using a cyclohexane/ethyl acetate mixture (8/2, v/v) as the eluent (yield=90%).

Preparation 3

(2,3-Dihydro-1,4-benzodioxin-6-yl)diphenylphosphine, Compound IVA.1

11 g of compound V and 30 ml of anhydrous tetrahydrofuran are placed under argon and cooled to −78° C. 25.6 ml of 2.2 M n-butyllithium in dioxane are added dropwise and the reaction mixture is then stirred at −78° C. for 1 hour. 10.4 ml of chlorodiphenylphosphine are then added dropwise, the temperature being maintained at −60° C. The temperature of the reaction mixture then rises slowly to 0° C. and 20 ml of saturated ammonium chloride solution are added at 0° C. The organic phase is then washed with 2 times 20 ml of saturated sodium chloride solution, dried over magnesium sulfate and filtered and the solvents are evaporated off under reduced pressure to give an orange oil, which crystallizes. The solid is subsequently washed with hot hexane and then filtered off (yield=90%).

$^1H$ NMR (200 MHz) $CDCl_3$: 4.26 (4H, m); 6.80–6.84 (2H, m); 6.85 (1H; d: J=4 Hz); 7.32 (10H, m) $^{31}P$ NMR (162 MHz) $CDCl_3$: −4.66 ppm Preparation 4

(2,3-Dihydro-1,4-benzodioxin-6-yl)diphenylphosphine oxide, Compound IIIA.1

8 ml of 30% aqueous hydrogen peroxide solution are added dropwise to a suspension of 16.3 g of compound IVA.1 in 60 ml of methanol, the temperature of the reaction mixture being maintained below 40° C. After stirring for one hour, 14 ml of 30% aqueous sodium sulfite solution are added. Stirring is maintained for 1 hour and 9 ml of 1 N aqueous hydrochloric acid solution are then added. The solution is concentrated at 40° C. and the aqueous residue is extracted with 50 ml of dichloromethane. The organic phase is dried over magnesium sulfate and the solvents are evaporated off under reduced pressure to give a yellow oil, which crystallizes. The solid obtained is washed with hot hexane and then filtered off (quantitative yield).

EI mass spectrum: $M^+=335$ $^1H$ NMR (200 MHz) $CDCl_3$: 4.26 (4H, m); 6.95 (1H, dd: J=11.8 Hz, J=3.1 Hz); 7.09–7.18 (2H, m); 7.42–7.54 (6H, m); 7.61–7.72 (4H, m) $^{31}P$ NMR (162 MHz) $CDCl_3$: 30.1 ppm Preparation 4 bis (2,3-Dihydro-1,4-benzodioxin-6-yl)diphenylphosphine oxide, Compound IIA.1

100.0 g of 6-bromo-2,3-dihydro-1,4-benzodioxin diluted in 200 ml of anhydrous THF are added over about 1 hour, under nitrogen, to a suspension of 12.4 g of magnesium in 31 ml of anhydrous THF, the temperature being maintained below 60° C. After the reaction mixture has been maintained at 60° C. for 2 hours, 107.7 g of chlorodiphenylphosphine are added over 3 hours without exceeding 10° C. in the reaction medium. After the temperature has been maintained at 20° C. for 18 hours, 35 ml of methanol are added. The reaction medium is stirred for one hour and then cooled to 0° C. 30 ml of 35% hydrogen peroxide are then added without exceeding 5° C. in the reaction mixture. After the temperature has been maintained at 20° C. for 2 hours and the solvents have been evaporated off under reduced pressure, the solid obtained is dissolved in 900 ml of hot isopropyl acetate, then washed successively with 3 times 200 ml of 1 N HCl, 150 ml of 1 N aqueous potassium carbonate solution and 150 ml of water and then dried over magnesium sulfate. After 500 ml of solvent have been evaporated off under reduced pressure, the reaction mixture is cooled to 0° C. and filtered and the solid is rinsed with 2 times 30 ml of isopropyl acetate. After drying for 72 hours at 20° C. under reduced pressure, 113 g of a creamy-white solid are obtained (yield=72%).

Preparation 5
(S)-[5,5'-bi(2,3-dihydro-1,4-benzodioxin)-6,6'-diyl]bis(diphenylphosphine oxide), Compound IIA.1

30 g of compound IIIA.1 and 600 ml of anhydrous tetrahydrofuran are degassed, placed under argon and then cooled to −100° C. with the aid of a cryostat. 65 ml of a 1.5 M solution of tert-butyllithium in pentane are added dropwise at −100° C. The reaction mixture is brought to −70° C. over 30 minutes and then stirred at this temperature for 3 hours 30 minutes. 19.8 g of anhydrous iron trichloride are then added all at once under a stream of argon. The reaction mixture is then slowly brought to room temperature and stirred for 12 hours. It is concentrated at 60° C. and 50 ml of 1 N aqueous sodium hydroxide solution and 500 ml of dichloromethane are added. The precipitate obtained is filtered off on Celite and then rinsed with 100 ml of dichloromethane. The organic phase is washed with 50 ml of water and 50 ml of saturated aqueous sodium chloride solution and dried over magnesium sulfate. After the solvents have been evaporated off under reduced pressure, the solid obtained is dissolved in 150 ml of chloroform, and a solution of 12 g of (−)-L-dibenzoyltartaric acid in 180 ml of ethyl acetate is then added. A precipitate appears after a few minutes. This precipitate is filtered off and then suspended in 200 ml of dichloromethane, and 100 ml of 1 N aqueous potassium hydroxide solution are added. The reaction mixture is stirred at room temperature for 30 minutes, after which the organic phase is separated off, washed with 50 ml of water and 50 ml of saturated aqueous sodium chloride solution and then dried over magnesium sulfate. The solvents are then evaporated off under reduced pressure (yield=50%).

$^1$H NMR (200 MHz) CDCl$_3$: 3.42 (2H, m); 3.69 (2H, m); 3.92 (2H, m); 4.06 (2H, m); 6.65 (2H, dd); 6.77 (dd); 7.26–7.56 (16H, m); 7.68 (4H, m) $^{31}$P NMR (162 MHz) CDCl$_3$: 30.97 ppm CI mass spectrum: MH$^+$=671 Melting point>260° C. $[\alpha]_D^{20}$ (CHCl$_3$, C=1)=−140°

An X-ray structure of the complex of compound IIA.1 with L-dibenzoyltartaric acid revealed the (S) absolute configuration.

An analogous procedure is used to prepare compound IIA.2: (R)-[5,5'-bi(2,3-dihydro-1,4-benzodioxin)-6,6'-diyl]bis(diphenylphosphine oxide) $[\alpha]_D^{20}$ (CHCl$_3$, C=1)=+143°

Preparation 6
(2,2-Difluoro-1,3-benzodioxol-5-yl)diphenylphosphine oxide, Compound IIIA.2

90.1 g of 5-bromo-2,2-difluoro-1,3-benzodioxole diluted in 168 ml of anhydrous THF are added over 2 hours, under nitrogen, to a suspension of 10.2 g of magnesium in 25.2 ml of anhydrous THF, the temperature being maintained at 60° C. After the reaction mixture has been maintained at room temperature for 3 hours, 90 g of chlorodiphenylphosphine oxide are added over 2 hours without exceeding 20° C. in the reaction mixture. After the reaction mixture has been maintained at 20° C. for 19 hours, it is hydrolyzed with 27 ml of water and 135 ml of 1 N HCl and then extracted with 270 ml of ethyl acetate. After decantation and phase separation, the organic phase is washed successively with 135 ml of 1 N HCl, 135 ml of saturated aqueous potassium bicarbonate solution and 135 ml of water and then dried over sodium sulfate. The solvents are evaporated off under reduced pressure to give 128 g of a brown viscous oil. This oil is purified by filtration on silica using an ethyl acetate/heptane mixture (varying from 50/50 to 100/0, v/v) as the eluent (brown oil, 90 g, yield=66%).

CI mass spectrum: MH$^+$=359 $^1$H NMR (300 MHz) CDCl$_3$: 7.70–7.41 (11H, m); 7.37 (1H, dd); 7.16 (1H, dd)

Preparation 7
(2,2-Difluoro-4-iodo-1,3-benzodioxol-5-yl)diphenylphosphine oxide, Compound IIIC.1

96.6 ml of a 2.5 M solution of butyllithium in hexane are added over 40 minutes at 0° C., under nitrogen, to a solution of 35.5 ml of diisopropylamine diluted in 150 ml of anhydrous THF. After stirring for 15 minutes at 0° C., the solution is added slowly over 1 hour, under nitrogen, to a solution of 82.5 g of compound IIIA.2 diluted in 600 ml of anhydrous THF at −78° C., and stirring is then maintained at −78° C. for 50 minutes. A solution of 60.9 g of iodine diluted in 250 ml of anhydrous THF is added over one hour to the previous solution at −78° C. The reaction mixture is then brought slowly to room temperature and subsequently stirred for 20 hours. It is then cooled to 0° C. and filtered and the solid is rinsed with 3×20 ml of THF. After drying for 5 hours at 40° C. under reduced pressure, 97.6 g of a creamy-white solid are obtained (yield=87.5%).

EI mass spectrum: M$^+$=484 $^1$H NMR (250 MHz) CDCl$_3$: 7.73–7.48 (10H, m); 7.04–6.96 (2H, m)

Preparation 8
(R,S)-[4,4'-bi(2,2-difluoro-1,3-benzodioxole)-5,5'-diyl]bis(diphenylphosphine oxide), Racemic Compound IIA.3

30 g of compound IIIC.1, 11.8 g of copper powder and 150 ml of DMF are heated at 130° C. for 4 hours. The reaction mixture is subsequently brought to room temperature, filtered and then concentrated. The brown oil obtained is subsequently diluted in 300 ml of dichloromethane, then washed successively with 100 ml of saturated aqueous ammonium chloride solution and 100 ml of water and dried over magnesium sulfate. The yellow solid obtained is then recrystallized from 250 ml of methanol at 0° C. and dried under reduced pressure to give 15.2 g of a white solid (yield=68.7%).

CI mass spectrum: M$^+$=715 $^1$H NMR (300 MHz) CDCl$_3$: 7.66–7.25 (20H, m); 7.03–7.00 (4H, m)

Compound IIA.3 is then resolved by chromatography on a chiral phase column marketed under the name Chirose® C3 to give the optically pure (S) and (R) enantiomers.

Preparation 9
Diphenyl (2,3-dihydro-1,4-benzodioxin-6-yl)phosphonate (Compound IIIB.1)

602 mg (25.6 mM) of activated magnesium and 1 ml of anhydrous tetrahydrofuran (THF) are placed in a three-necked round-bottom flask under argon. Two drops of 1,3-dibromopropane are added and 5 g (23.3 mM) of compound V dissolved in 10 ml of THF are then added, the temperature being maintained at 0° C. The reaction mixture is stirred for 2 hours at room temperature and then for 1 hour at the reflux point of the solvent. The magnesium compound formed is then added slowly to a solution of 4.84 ml (23.25 mM) of diphenylphosphinic chloride in 5 ml of THF, cooled to −5° C. beforehand. The solution is stirred overnight at room temperature and then concentrated under reduced pressure. The residue is taken up in 20 ml of ethyl acetate and stirred with 10 ml of normal hydrochloric acid solution for 30 minutes. The aqueous phase is extracted with ethyl acetate and the combined organic phases are washed with water, dried over magnesium sulfate and concentrated under reduced pressure. The oil obtained is purified by chromatography on silica gel using a cyclohexane/ethyl acetate mixture (7/3, v/v) as the eluent to give 5 g of the expected product in the form of a pinkish-white solid (yield=59%).

$^1$H NMR (200 MHz, CDCl$_3$): δ=4.25–4.32 (m, 4H); 6.95 (dd, J=5.1, 8.1 Hz, 1H); 7.10–7.35 (m, 10H); 7.39–7.43 (m, 1H); 7.47 (ddd, 1H) $^{13}$C NMR (50 MHz, CDCl$_3$): δ=64.1; 64.5; 117.7 (d, J=18.5 Hz); 120.5 (d, J=4.5 Hz); 121.6 (d, J=12.7 Hz); 124.9; 125.9 (d, J=10.6 Hz); 129.6; 143.5 (d, J=22.2 Hz); 147.9; 150.5 (d, J=7.4 Hz) $^{31}$P NMR (162 MHz, CDCl$_3$): δ=13.11 Mass spectrum (EI): M$^+$=368

Preparation 10

Diethyl (2,3-dihydro-1,4-benzodioxin-6-yl)phosphonate (Compound IIIB.2)

20 g (92.8 mM) of the compound obtained according to Preparation 1 and 1.2 g (9.28 mM) of nickel chloride are placed in a round-bottom flask equipped with a distillation apparatus. The mixture is stirred and brought to 160° C. and 18.8 ml (111.4 mM) of triethyl phosphite are added dropwise. The reaction mixture is stirred at 160° C. for one hour after the addition has ended, while the bromoethane formed by the reaction is collected by distillation. The reaction medium is then cooled and 50 ml of ethyl ether and 50 ml of ethyl acetate are added. The suspension obtained is filtered and the filtrate is concentrated under reduced pressure. The residue is then purified by chromatography on silica gel using ethyl acetate as the eluent to give 25 g of the expected product in the form of a colorless oil (quantitative yield).

$^1$H NMR (400 MHz, CDCl$_3$): δ=1.24 (t, J=7.0 Hz, 6H); 4.01 (qd, J=7.0, 9.9 Hz, 4H); 4.20–4.23 (m, 4H); 6.86 (dd, J=8.1, 4.6 Hz, 1H); 7.19–7.22 (m, 2H) $^{13}$C NMR (50 MHz, CDCl$_3$): δ=16.1; 61.8; 64.0; 64.4; 117.5 (d, J=17.5 Hz); 120.9 (d, J=12.0 Hz); 125.3 (d, J=10.0 Hz); 125.5; 143.4 (d, J=20.8 Hz); 147.2 $^{31}$P NMR (162 MHz, CDCl$_3$): δ=20.20 Mass spectrum (EI): M$^+$=272

Preparation 11

Tetraphenyl [5,5'-bi(2,3-dihydro-1,4-benzodioxin)-6,6'-diyl]-diphosphonate (Compound IIB.1)

A solution of 0.675 ml (3.97 mM) of tetramethylpiperidine in 5 ml of THF is prepared and cooled to −78° C. and 1.32 ml (3.24 mM) of a 2.4 M solution of n-butyllithium in hexane are added. The solution is stirred for 30 min at −15° C. and then added to a solution of 1 g (2.27 mM) of compound IIIB.1 in 5 ml of THF, cooled to −78° C. The mixture is stirred for 1 hour at −78° C. and 570 mg (3.5 mM) of anhydrous ferric chloride are then added. The mixture is stirred overnight at room temperature and then concentrated under reduced pressure. The residue is taken up in 30 ml of dichloromethane and stirred for 30 min in the presence of 15 ml of N sodium hydroxide solution. The mixture is filtered and the organic phase is separated off and washed successively with 15 ml of water, 15 ml of N hydrochloric acid solution, 10 ml of water and 10 ml of saturated sodium chloride solution. This organic phase is then dried over magnesium sulfate and concentrated under reduced pressure. The residue is purified by chromatography on silica gel using a cyclohexane/ethyl acetate mixture (1/1, v/v) as the eluent to give 200 mg of the expected product in the form of a pale yellow solid (yield=20%).

$^1$H NMR (200 MHz, CDCl$_3$): δ=3.80–3.90 (m, 2H); 3.95–4.10 (m, 4H); 4.144.30 (m, 2H); 6.88 (dd, J=8.2, 17.7, 8H); 7.00–7.22 (m, 14H); 7.72 (dd, J=14.5, 8.4 Hz, 2H) $^{13}$C NMR (50 MHz, CDCl$_3$): δ=63.8; 64.2; 116.8 (d, J=18.5 Hz); 120.8; 124.5; 126.9 (d, J=9.8 Hz); 129.2; 142.3 (d, J=22.1 Hz); 147.6; 150.5 (d, J=8.1 Hz) $^{31}$P NMR (162 MHz, CDCl$_3$): δ=11.68 Mass spectrum (CI): (M+H)$^+$=735

Preparation 12

Tetraethyl [5,5'-bi(2,3-dihydro-1,4-benzodioxin)-6,6'-diyl]-diphosphonate (Compound IIB.2)

A solution of 6.72 ml (44.4 mM) of TMEDA (tetramethylethylenediamine) and 5 g (18.5 mM) of compound IIB.2 in 50 ml of THF is prepared and 20.2 ml (22.2 mM) of a 1.1 M solution of sec-butyllithium in hexane are added at −60° C. The solution is stirred for 2 h at −60° C. and 3.91 g (24 mM) of anhydrous ferric chloride are then added all at once at −60° C. The mixture is stirred overnight at room temperature. It is concentrated under reduced pressure and taken up in 100 ml of dichloromethane and 30 ml of 1 N sodium hydroxide solution and the suspension is stirred for 30 min. After filtration, the organic phase is washed with water and then successively with 30 ml of N hydrochloric acid solution, 30 ml of water and 30 ml of saturated sodium chloride solution, dried over magnesium sulfate, filtered and concentrated under reduced pressure. The solid residue is crystallized (ethyl ether/hexane, 1:1) to give 1.6 g of the expected compound in the form of a white solid (yield=32%).

$^1$H NMR (400 MHz, CDCl$_3$): δ=1.13 (q, J=7.0 Hz, 12H); 3.69–3.80 (m, 2H); 3.85–3.92 (m, 6H); 4.14–4.17 (m, 4H); 4.22–4.24 (m, 4H); 6.90 (dd, J=4.0, 8.3 Hz, 2H); 7.41 (dd, J=13.8, 8.5 Hz, 2H) $^{13}$C NMR (50 MHz, CDCl$_3$): δ=16.1; 61.2 (d, J=8.0 Hz); 63.9; 64.2; 116.2 (d, J=17.3 Hz); 125.2; 125.9 (d, J=9.1 Hz); 128.8 (d, J=12.1 Hz); 141.8 (d, J=20.8 Hz); 146.5 $^{31}$P NMR (162 MHz, CDCl$_3$): δ=19.13 Mass spectrum (EI): M$^+$=542

Preparation 13

[5,5'-Bi(2,3-dihydro-1,4-benzodioxin)-6,6'-diyl] diphosphonyl tetrachloride (Compound IIC)

2 g (3.69 mM) of compound IIB.2, 16 ml of thionyl chloride and 0.4 ml of dimethylformamide are introduced into a round-bottom flask fitted with a condenser, under an argon atmosphere, and refluxed (80–90° C.) for 4.5 h. The solution turns bright yellow. The mixture is concentrated under reduced pressure and dried to give a dark orange solid (needles), which can be kept in the refrigerator under an argon atmosphere until used directly in the next step.

$^1$H NMR (400 MHz, CDCl$_3$): δ=4.17–4.36 (m, 8H); 7.06 (dd, J=8.7, 5.8 Hz, 2H); 7.54 (dd, J=20.0, 8.7 Hz, 2H) $^{31}$P NMR (162 MHz, CDCl$_3$): δ=34.74

Preparation 14

[5,5'-Bi(2,3-dihydro-1,4-benzodioxin)-6,6'-diyl]bis[di(4-methylphenyl)-phosphine oxide], Compound IIA.4

19.9 ml (36.9 mM) of a 1.85 M solution of n-butyllithium in hexane are added at −78° C. to a solution of 6.3 g (36.9 mM) of 4-bromotoluene in 50 ml of THF. A white suspension appears. The solution is stirred for 1 h at −78° C. and then added to a solution of 1.86 g (3.69 mM) of compound IIC in 10 ml of THF. The solution turns dark brown. The mixture is subsequently brought to room temperature and then stirred for 1 h at 50° C. 20 ml of saturated ammonium chloride solution are added and the organic phase is washed with water and then with saturated sodium chloride solution, dried over magnesium sulfate and concentrated under reduced pressure. The residue is purified by chromatography on silica gel using an ethyl acetate/methanol mixture (9/1, v/v) as the eluent to give 1.32 g of the expected compound in the form of a beige solid (yield=50% over two steps).

$^1$H NMR (400 MHz, CDCl$_3$): δ=2.30 (s, 6H); 2.38 (s, 6H); 3.57 (ddd, J=2.3, 7.2, 11.4 Hz, 2H); 3.75 (ddd, J=2.4, 4.3, 11.6 Hz, 2H); 3.97 (ddd, J=2.3, 4.2, 11.2 Hz, 2H); 4.09 (ddd, J=2.6, 7.2, 11.1 Hz, 2H); 6.65 (dd, J=8.5, 13.2 Hz, 2H); 6.74 (dd, J=3.0, 8.4 Hz, 2H); 7.04 (dd, J=2.4, 8.0 Hz, 4H); 7.20 (dd, J=2.1, 8.0 Hz, 4H); 7.32 (dd, J=8.0, 11.8 Hz, 4H); 7.53 (dd, J=8.0, 11.4 Hz, 4H) $^{13}$C NMR (50 MHz, CDCl$_3$): δ=21.4; 63.4; 64.0; 115.8; 126.5 (d, J=13.3 Hz); 128.4 (d, J=12.3 Hz); 132.1 (d, J=10.4 Hz); 132.4; 132.9; 135.8; 140.9; 142.5; 145.7 $^{31}$P NMR (162 MHz, CDCl$_3$): δ=30.95 Mass spectrum (CI): (M+H)$^+$=727

Preparation 15

[5,5'-Bi(2,3-dihydro-1,4-benzodioxin)-6,6'-diyl]bis[bis(3, 5-dimethylphenyl)phosphine oxide], Compound IIA.5

This compound is obtained by following an analogous procedure to Preparation 13, starting from 5-bromo-m-xylene.

$^1$H NMR (400 MHz, CDCl$_3$): δ=2.12 (s, 12H); 2.31 (s, 12H); 3.63–3.66 (m, 2H); 3.75–3.79 (m, 2H); 4.00–4.04 (m, 2H); 4.08–4.13 (m, 2H); 6.72–6.75 (m, 2H); 6.96 (s, 2H); 7.11 (d, J=12.7 Hz, 6H); 7.29 (d, J=12.0 Hz, 4H) $^{13}$C NMR (50 MHz, CDCl$_3$): δ=21.0; 21.3; 63.4; 63.9; 115.9 (d, J=15.4 Hz); 126.6 (d, J=12.9 Hz); 129.8; 132.5; 134.1; 136.1; 137.1; 141.0 (d, J=14.9 Hz); 145.5 $^{31}$P NMR (162 MHz, CDCl$_3$): δ=31.78 Mass spectrum (CI): (M+H)$^+$=783

EXAMPLE 1

(S)-[5,5'-bi(2,3-dihydro-1,4-benzodioxin)-6,6'-diyl]bis (diphenylphosphine), Compound I.1

2.12 ml of tributylamine and then 780 μl of trichlorosilane are added to 500 mg of compound IIA.1 and 5 ml of degassed distilled xylene, placed under argon. The reaction mixture is heated at 140° C. for 12 hours. When it has returned to room temperature, 5 ml of 4 N aqueous sodium hydroxide solution are added. The reaction mixture is then stirred at room temperature for 30 minutes and 15 ml of dichloromethane are added. The organic phase is washed with 5 ml of distilled water and then with 5 ml of saturated aqueous sodium chloride solution and subsequently concentrated under reduced pressure. 10 ml of methanol are then added and the white precipitate obtained is filtered off under argon, washed with 10 ml of methanol and then dried under reduced pressure for 4 hours (yield=91%).

$[α]_D^{20}$ (benzene, C=0.1)=–44°

The following compounds are prepared in the same manner:

(R)-[5,5'-bi(2,3-dihydro-1,4-benzodioxin)-6,6'-diyl]bis (diphenylphosphine), Compound I.2

$^1$H NMR (200 MHz) CDCl$_3$: 3.35 (2H, m); 3.83 (4H, m); 4.13 (2H, m); 6.62 (2H, dd: J=8 Hz, J=3 Hz); 6.85 (2H, d: J=8 Hz); 7.09 (4H, m); 7.23 (8H, m); 7.31 (8H, m) $^{31}$P NMR (162 MHz) CDCl$_3$: –14.3 ppm $[α]_D^{20}$ (benzene, C=0.1)=+44°

(R)-[4,4'-bi(2,2-difluoro-1,3-benzodioxole)-5,5'-diyl]bis (diphenylphosphine), Compound I.3

$[α]_D^{20}$ (CH$_3$OH, C=0.5)=+48°

(S)-[4,4'-bi(2,2-difluoro-1,3-benzodioxole)-5,5'-diyl]bis (diphenylphosphine), Compound I.4

$[α]_D^{20}$ (CH$_3$OH, C=0.5)=–49°

[5,5'-Bi(2,3-dihydro-1,4-benzodioxin)-6,6'-diyl]bis[di(4-methylphenyl)-phosphine], Compound I.5

$^1$H NMR (200 MHz, CDCl$_3$): δ=2.29 (s, 6H); 2.33 (s, 6H); 3.32–3.44 (m, 2H); 3.74–3.94 (m, 4H); 4.034.18 (m, 2H); 6.62 (m, 2H); 6.82 (d, J=8.4 Hz, 2H); 6.87–7.23 (m, 16H)

[5,5'-Bi(2,3-dihydro-1,4-benzodioxin)-6,6'-diyl]bis[bis(3, 5-dimethylphenyl)phosphine], Compound I.6

$^1$H NMR (400 MHz, CDCl$_3$): δ=2.12 (s, 12H); 2.25 (s, 12H); 3.47 (ddd, J=2.3, 4.3, 12.0, 2H); 3.83 (ddd, J=2.1, 6.9, 11.6, 2H); 3.95 (ddd, J=2.2, 4.5, 11.4, 2H); 4.14 (ddd, J=2.3, 7.2, 11.2, 2H); 6.63–6.67 (m, 6H); 6.80 (m, 4H); 6.90 (d, J=8.1 Hz, 6H) $^{31}$P NMR (162 MHz, CDCl$_3$): δ=–14.52

EXAMPLE 2

Compound VII.1: Complex [Ru$_2$Cl$_5$L$_2$]-[(C$_2$H$_5$)$_2$NH$_2$]$^+$ where L=Compound I.1

50 mg of bis(benzenedichlororuthenium), 128 mg of compound I.1 and 21.6 mg of diethylamine hydrochloride in 10 ml of tetrahydrofuran are refluxed for 16 hours. The solvents are then evaporated off under reduced pressure. The solid obtained is dried under reduced pressure.

$^{31}$P NMR (162 MHz) CDCl$_3$: 51.1 (d); 54.4 (d) J=38 Hz

EXAMPLE 3

Compound VI.1: Complex [LRuCl$_2$(pyridine)$_2$] where L=Compound I.2

42.2 mg of (norbornadiene)RuCl$_2$(pyridine)$_2$, 63.9 mg of compound I.2 and 15 ml of degassed anhydrous CH$_2$Cl$_2$ are then added and the reaction mixture is stirred for 12 hours under argon at room temperature. The solution is concentrated and dried under reduced pressure to give 96 mg of an orange-yellow solid.

$^{31}$P NMR (162 MHz) CDCl$_3$: 40.9 ppm

EXAMPLE 4

Compound VI.2: Complex [LRuCl$_2$S-DPED] where L=Compound I.2

34 mg of [LRuCl$_2$(pyridine)$_2$] obtained in EXAMPLE 3, 7.4 mg of (S,S)-diphenylethylenediamine and 5 ml of degassed anhydrous CH$_2$Cl$_2$ are stirred for 2 hours under argon at room temperature. The solution is concentrated and dried under reduced pressure to give 96 mg of an orange-yellow solid.

$^{31}$P NMR (162 MHz) CDCl$_3$: 48.1 ppm

EXAMPLE 5

Compound VII.2: Complex [LRhcod]$^+$BF$_4^-$ where L=Compound I.2

50 mg of [Rh(cod)$_2$]+BF$_4$ and 58.6 mg of compound I.2 are placed in a Schlenk tube. The system is placed under argon by means of 3 successive vacuum/argon purges. 10 ml of THF are then added and the reaction mixture is stirred for 30 minutes. After evaporation of the solvent, the residue obtained is dried under vacuum to give 110 mg of a yellow powder.

EXAMPLE 6

Asymmetric Hydrogenation

General Methods:

a) with chiral ruthenium catalysts, prepared in situ, of the formula [LRuBr$_2$] where L=compound (I)

2.2 equivalents of a 0.16 N–0.19 N solution of hydrobromic acid in methanol are added dropwise to 3.2 mg of (1,5-cyclooctadiene)bismethylallylruthenium and 1.1 equivalents of compound (I) in 1 ml of acetone under argon. After stirring for 30 minutes at room temperature, the solvents are evaporated off under reduced pressure.

The substrate to be hydrogenated (1 mmol) is then dissolved in 2 ml of hydrogenation solvent (of the alcohol or halogenated type, such as dichloromethane) and placed in an autoclave in the presence of the catalyst under the desired hydrogen pressure and at the desired temperature.

b) with ruthenium trichloride

The substrate to be hydrogenated (1 mmol), dissolved in 2 ml of hydrogenation solvent, is added to 2.1 mg of ruthenium trichloride and 1.1 equivalents of compound (I). The hydrogenation is performed in an autoclave for the necessary time at the desired pressure and temperature.

c) with the complex described in EXAMPLE 2

The substrate to be hydrogenated (1 mmol), dissolved in 2 ml of hydrogenation solvent, is added to 3.6 mg of complex. The hydrogenation is performed in an autoclave for the necessary time at the desired pressure and temperature.

The catalysts according to the invention for stereoselective hydrogenation are useful for carrying out reductions of the following type:

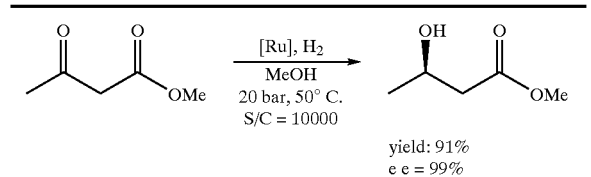

yield: 91%
e e = 99%

[Ru] = [LRuBr$_2$] where L = compound I2

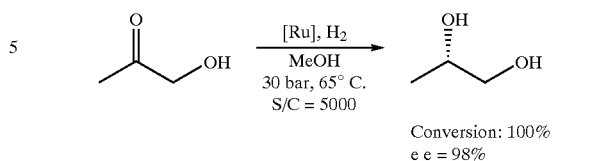

Conversion: 100%
e e = 98%

[Ru] = [Ru$_2$Cl$_5$L$_2$]$^-$[(C$_2$H$_5$)$_2$NH$_2$]$^+$ where L = compound I.1 (compound VII.1)

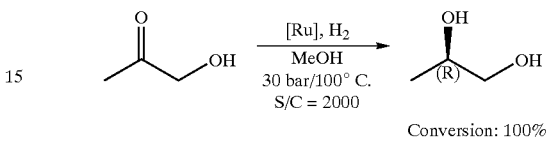

Conversion: 100%

| [Ru] | ee (%) (configuration) |
|---|---|
| [LRuBr$_2$] in situ | 98.5 (R) |
| Compound VII.1*: [Ru$_2$Cl$_5$L$_2$]$^-$[(C$_2$H$_5$)$_2$NH$_2$]$^+$ | 98.2 (R) |

*where L = compound I.2
S/C represents the substrate/catalyst weight ratio.

The enantiomeric excesses (ee) obtained by the hydrogenation of different substrates are shown in TABLE 1 below by way of example, the conditions used not being optimized (the letters indicated in the [Ru] column refer to the method of preparation of the catalyst).

TABLE 1

| Substrate | [Ru] | P (bar) | T (° C.) solvent | Time (h) | Ligand | ee (%) |
|---|---|---|---|---|---|---|
| methyl acetoacetate | (a) | 4 | 50 MeOH | 24 | I.2 | >99 (R) |
| methyl acetoacetate | (b) | 4 | 50 MeOH | 24 | I.1 | >99 (S) |
| methyl 3-oxopentanoate | (a) | 4 | 50 MeOH | 24 | I.2 | >99 (R) |
| ethyl 3-oxohexanoate | (a) | 4 | 50 EtOH | 24 | I.2 | >99 (R) |
| ethyl 5-methyl-3-oxohexanoate | (a) | 4 | 50 EtOH | 24 | I.2 | >99 (S) |
| diethyl (2-oxo-3-phenylpropyl)phosphonate | (b) | 20 | 50 EtOH | 64 | I.2 | >99 (S) |

TABLE 1-continued

| Substrate | [Ru] | P (bar) | T (° C.) solvent | Time (h) | Ligand | ee (%) |
|---|---|---|---|---|---|---|
| CH₃-CO-CH₂-CH₂-SPh (4-(phenylthio)-2-butanone) | (a) | 30 | 30 MeOH | 24 | I.2 | 98.5 (R) |
| CH₃-CO-CH₂-CO-CH₃ (2,4-pentanedione) | (a) | 20 | RT MeOH | 64 | I.2 | >99 (R, R) |
| CH₂=C(CH₂CO₂CH₃)(CO₂CH₃) (dimethyl itaconate) | (a) | 20 | 50 MeOH | 24 | I.1 | 93 (S) |
| CH₂=C(CH₂CO₂CH₃)(CO₂CH₃) (dimethyl itaconate) | (c) | 20 | 50 MeOH | 24 | I.1 | 91 (S) |
| N-benzoyl-3,4-dihydro-2-naphthylamine | (a) | 40 | 50 CH₂Cl₂/MeOH | 24 | I.2 | 91 (R) |
| Methyl phenylglyoxylate (PhCOCO₂CH₃) | (a) | 20 | 50 MeOH | 24 | I.1 | 91.5 (S) |
| Methyl acetoacetate (CH₃COCH₂CO₂CH₃) | (a) | 4 | 50 MeOH | 24 | I.3 | >99 (R) |
| Ethyl 3-methyl-2-oxobutanoate ((CH₃)₂CHCOCO₂Et) | (a) | 20 | 50 EtOH | 24 | I.1 | 94 (S) |
| Ethyl 2-thienylglyoxylate | (a) | 15 | 80 EtOH | 24 | I.1 | 63 (S) |
| Ethyl benzoylacetate (PhCOCH₂CO₂Et) | (a) | 10 | 80 EtOH | 24 | I.1 | 97 (S) |
| Ethyl 4,4,4-trifluoroacetoacetate (CF₃COCH₂CO₂Et) | (a) | 20 | 99 EtOH | 24 | I.1 | 49 (R) |
| Ethyl 4,4,5,5,5-pentafluoro-3-oxopentanoate (C₂F₅COCH₂CO₂Et) | (a) | 20 | 99 EtOH | 24 | I.1 | 63 (R) |

TABLE 1-continued

| Substrate | [Ru] | P (bar) | T (° C.) solvent | Time (h) | Ligand | ee (%) |
|---|---|---|---|---|---|---|
| hydroxyacetone (CH₃COCH₂OH) | (a) | 5 | 50 MeOH | 24 | I.1 | >99 (S) |
| diethyl (2-oxopropyl)phosphonate (CH₃COCH₂P(O)(OEt)₂) | (a) | 10 | 50 EtOH | 24 | I.1 | >99 (S) |
| ethyl 4,4,4-trifluoroacetoacetate (CF₃COCH₂CO₂Et) | (a) | 20 | 99 EtOH | 24 | I.4 | 70 (R) |
| ethyl 4,4,5,5,5-pentafluoro-3-oxopentanoate (C₂F₅COCH₂CO₂Et) | (a) | 20 | 99 EtOH | 24 | I.4 | 75 (R) |
| ethyl 4,4,5,5,6,6,6-heptafluoro-3-oxohexanoate (C₃F₇COCH₂CO₂Et) | (a) | 10 | 110 EtOH | 3 | I.4 | 80 (R) |
| hydroxyacetone (CH₃COCH₂OH) | (a) | 5 | 50 MeOH | 24 | I.4 | 96 (S) |
| ethyl 3-(2-fluorophenyl)-3-oxopropanoate | (a) | 10 | 80 EtOH | 3 | I.2 | 88 (S) |
| ethyl 3-(2-fluorophenyl)-3-oxopropanoate | (a) | 10 | 80 EtOH | 3 | I.3 | 89 (S) |
| ethyl 3-(pentafluorophenyl)-3-oxopropanoate | (a) | 10 | 80 EtOH | 3 | I.2 | 97 (S) |

EXAMPLE 7

Asymmetric 1,4-addition 1 ml of dioxane, 0.1 ml of distilled water and 0.4 mmol of cyclohexenone are added to 3.1 mg of Rh(acac)(C₂H₄)₂, 0.012 mmol of compound I.1 and 2 mmol of phenylboronic acid under argon. The reaction mixture is heated at 100° C. for 5 hours. After it has returned to room temperature, the solvents are evaporated off under reduced pressure. The residue obtained is dissolved in 20 ml of ethyl acetate, washed with 5 ml of saturated aqueous sodium hydrogencarbonate solution and then dried over sodium sulfate. The solvents are then evaporated off under reduced pressure. The product is purified by filtration on silica to isolate (S)-3-phenylcyclohexanone, which is characterized by the ¹H NMR spectrum below.

$^1$H NMR (200 MHz) CDCl₃: 1.84 (2H, m); 2.16 (2H, m); 2.46 (4H, m); 3.0 (1H, m); 7.21–7.45 (5H, m) Enantiomeric excess: 96% ee (determined by Lipodex A chiral GPC)

EXAMPLE 8

TABLE 2 below shows a comparison of the results of the hydrogenation of different substrates obtained on the one hand with the ruthenium complexes according to the invention and on the other hand with complexes of the type Ru-Binap, under the same operating conditions (temperature, pressure and solvent).

TABLE 2 shows a comparison of the results obtained in TABLE 1 with the complexes according to the invention and the results obtained with the corresponding complexes in which the ligand (1) according to the invention has been replaced by the ligand BINAP.

TABLE 2

| Substrate | [Ru] | Li-gand | ee (%) (I) | ee (%) BINAP |
|---|---|---|---|---|
| CH₃COCH₂CO₂CH₃ | (a) | (R) | >99 (R) | >99 (R) |
| CH₃CH₂COCH₂CO₂CH₃ | (a) | (R) | >99 (R) | >99 (R) |
| CH₃CH₂CH₂COCH₂CO₂CH₂CH₃ | (a) | (R) | >99 (R) | >99 (R) |
| (CH₃)₂CHCOCH₂CO₂CH₂CH₃ | (a) | (R) | >99 (S) | >99 (S) |
| PhCOCH₂P(O)(OCH₂CH₃)₂ | (b) | (R) | >99 (S) | 98 (S) |
| CH₃COCH₂CH₂SPh | (a) | (R) | 98.5 (R) | 96 (R) |
| PhCOCOCO₂CH₂CH₃ | (a) | (S) | 90 (S) | 82 (S) |
| CH₃COCH₂COCH₃ | (a) | (R) | >99 (R, R) d.e. > 99 | >99 (R, R) d.e. = 95 |
| CH₂=C(CO₂CH₃)CH₂CO₂CH₃ | (a) | (S) | 93 (S) | 90 (S) |
| N-(dihydronaphthalen-2-yl)benzamide | (a) | (R) | 91 (R) | 90 (R) |
| (CH₃)₂CHCOCOCO₂Et | (a) | (S) | 94 (S) | 84 (S) |
| 2-thienyl-COCOCO₂Et | (a) | (S) | 63 (S) | 56 (S) |
| PhCOCH₂CO₂Et | (a) | (S) | 97 (S) | 88 (S) |
| CF₃COCH₂CO₂Et | (a) | (S) | 49 (R) | 23 (R) |
| C₂F₅COCH₂CO₂Et | (a) | (S) | 63 (R) | 44 (R) |
| CH₃COCH₂OH | (a) | (S) | 99 (S) | 92 (S) |

What is claimed is:

1. A compound, in optically pure or racemic form, of formula (I):

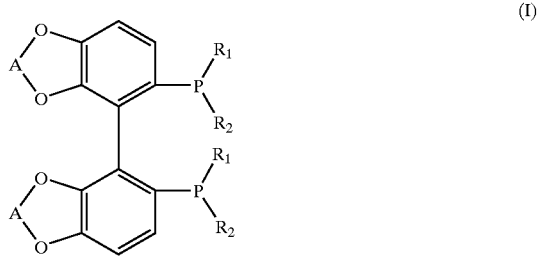

(I)

in which:

$R_1$ and $R_2$ each independently are:
  a $(C_5-C_7)$cycloalkyl group, a phenyl group optionally substituted by one or more $(C_1-C_4)$alkyl, $(C_1-C_4)$alkoxy or di$(C_1-C_4)$alkylamino groups or by a halogen atom, or
  a 5-membered heteroaryl group; and A is an ethylene group ($CH_2$—$CH_2$) or a $CF_2$ group.

2. The compound of formula (I) according to claim 1, wherein $R_1$ and $R_2$ are identical.

3. The compound of formula (I) according to claim 2, wherein $R_1$ and $R_2$ are a phenyl group.

4. Intermediates of formula (IIA) useful for the preparation of the compound of formula (I) according to claim 1:

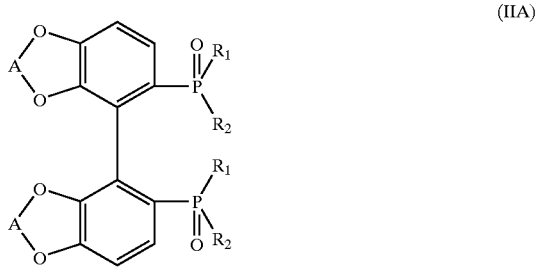

(IIA)

in which $R_1$, $R_2$ and A are as defined for (I) in claim 1.

5. Intermediates of formula (IIB) useful for the preparation of the compound of formula (I) according to claim 1:

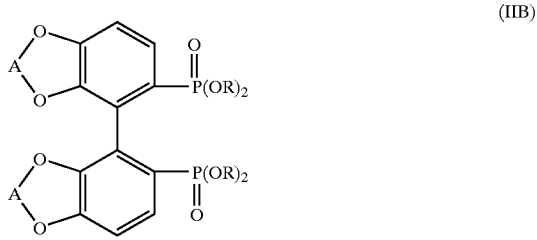

(IIB)

in which A is as defined for (I) in claim 1 and R is a ($C_1$–$C_4$)alkyl group or an optionally substituted phenyl group.

6. Intermediates of formula (IIIA) useful for the preparation of the compound of formula (I) according to claim 1:

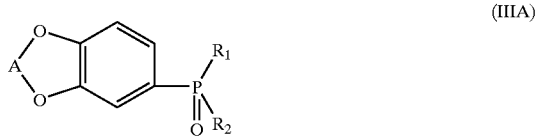

(IIIA)

in which $R_1$, $R_2$ and A are as defined for (I) in claim 1.

7. Intermediates of formula (IIIC) useful for the preparation of the compound of formula (I) according to claim 1:

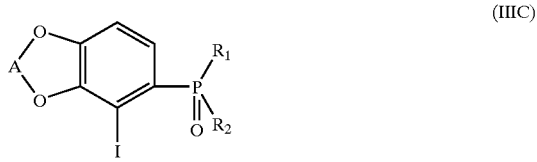

(IIIC)

in which $R_1$, $R_2$ and A are as defined for (I) in claim 1.

8. Intermediates of formula (IVA) useful for the preparation of the compound of formula (I) according to claim 1:

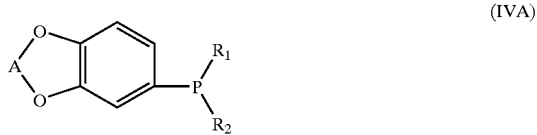

(IVA)

in which $R_1$, $R_2$ and A are as defined for (I) in claim 1.

9. A chiral metal catalyst, which comprises a compound of formula (I) according to claim 1 as a ligand.

10. The chiral metal catalyst according to claim 9, wherein said compound of formula (I) is in optically pure form.

11. The chiral metal catalyst according to claim 9, wherein the metal is selected from the group consisting of rhodium, ruthenium, iridium, palladium, copper and nickel.

12. The chiral metal catalyst according to claim 11 of formula (VI):

$$M_m L_n X_p S_q \qquad (VI)$$

in which:

M is a metal selected from the group consisting of rhodium, ruthenium, iridium, palladium, nickel and copper;

L is a compound of formula (I); and

X, S, m, n, p and q are defined as follows:
  if M=Rh, then X=Cl, Br or I; m=n=p=2; q=0;
  if M=Ru, then: X=—OC(O)CH$_3$; m=n=1; p=2; q=0;
    or X=Br; m=n=1; p=2; q=0;
    or X=Cl; S=N(CH$_2$CH$_3$)$_3$; m=n=2; p=4; q=1;
    or X=methylallyl; m=n=1; p=2; q=0;
    or X=Cl; S=pyridine; m=n=1; p=q=2;
    or X=Cl; S=chiral 1,2-diamine; m=n=1; p=q=2 or p=2, q=1;
  if M=Ir, then X=Cl, Br or I; m=n=p=2; q=0;
  if M=Pd, then: X=Cl; m=n=1; p=2; q=0;
    or X=π-allyl; m=n=p=2; q=0;
  if M=Ni, then X=Cl, Br or I; m=n=1; p=2; q=0.

13. The chiral metal catalyst according to claim 11 of formula (VII):

$$[M_r L_s Z_t W_u] Y_v \qquad (VII)$$

in which:

M is a metal selected from the group consisting of rhodium, ruthenium, iridium, palladium and copper;

L is a compound of formula (I); and

Z, W, r, s, t, u and v are defined as follows:
  if M=Rh, then Z=1,5-cyclooctadiene or norbornadiene; Y=BF$_4$, ClO$_4$, PF$_6$, OTf or BPh$_4$; r=s=t=v=1; u=0;
  if M=Ru, then: Z=Cl, Br or I; W=benzene or p-cymene; Y=Cl, Br or I; r=s=t=u=v=1;
    or Y=BF$_4$, ClO$_4$, PF$_6$ or BPh$_4$; r=s=1; t=u=0; v=2;
    or Z=Cl; Y=NH$_2$(C$_2$H$_5$)$_2$; r=s=2; t=5; u=0; v=1;
  if M=Ir, then Z=1,5-cyclooctadiene or norbornadiene; Y=BF$_4$, ClO$_4$, PF$_6$ or BPh$_4$; r=s=v=1; t=1; u=0;
  if M=Pd, then Y=BF$_4$, ClO$_4$, PF$_6$ or BPh$_4$; r=s=v=1; t=u=0;
  if M=Cu, then Y=PF$_6$ or ClO$_4$; r=s=v=1; t=u=0.

14. The catalyst of formula (VI) according to claim 12, wherein M=Ru and
  X=Br; m=n=1; p=2; q=0;
    or X=Cl; S=N(CH$_2$CH$_3$)$_3$; m=n=1; p=4; q=1;
    or X=Cl; S=pyridine; m=n=1; p=q=2.

15. The catalyst of formula (VII) according to claim 13, wherein M=Rh and Z=1,5-cyclooctadiene or norbornadiene; Y=BF$_4$, ClO$_4$, PF$_6$, OTf or BPh$_4$; r=s=t=v=1; u=0.

16. A catalytic hydrogenation process, which comprises hydrogenating a substrate in the presence of a catalyst according to claim 9.

17. A catalytic hydrogenation process, which comprises hydrogenating a substrate in the presence of a catalyst according to claim 10.

18. A catalytic hydrogenation process, which comprises hydrogenating a substrate in the presence of a catalyst according to claim 11.

19. A catalytic hydrogenation process, which comprises hydrogenating a substrate in the presence of a catalyst according to claim 12.

20. A catalytic hydrogenation process, which comprises hydrogenating a substrate in the presence of a catalyst according to claim 13.

21. A catalytic hydrogenation process, which comprises hydrogenating a substrate in the presence of a catalyst according to claim 14.

22. A catalytic hydrogenation process, which comprises hydrogenating a substrate in the presence of a catalyst according to claim 15.

23. A process for catalyzing the asymmetric reaction of a starting compound into an end compound, which comprises carrying out the reaction in the presence of a catalyst according to claim 9.

* * * * *